United States Patent [19]

Cherkassky

[11] Patent Number: 4,602,623
[45] Date of Patent: Jul. 29, 1986

[54] METHOD OF DELIVERING A FETUS

[76] Inventor: Michael Cherkassky, 301 The Height Dr. #D, Fort Worth, Tex. 76112

[21] Appl. No.: 566,982

[22] Filed: Dec. 30, 1983

[51] Int. Cl.<sup>4</sup> .......................................... A61B 17/42
[52] U.S. Cl. .................................... 128/323; 128/361
[58] Field of Search ................ 128/323, 324, 361, 1 R

[56] References Cited

U.S. PATENT DOCUMENTS

| | | | |
|---|---|---|---|
| 1,782,814 | 11/1930 | Froehlich | 128/361 |
| 2,842,134 | 7/1958 | Post | 128/361 |
| 3,150,662 | 9/1964 | Carlson et al. | 128/361 X |
| 3,516,406 | 6/1970 | Jensen | 128/361 |
| 3,592,198 | 10/1971 | Evans | 128/352 |
| 3,626,949 | 12/1971 | Shute | 128/344 |
| 4,136,679 | 1/1979 | Martinez et al. | 128/1 R |

FOREIGN PATENT DOCUMENTS

| | | | |
|---|---|---|---|
| 2233840 | 1/1974 | Fed. Rep. of Germany | 128/361 |
| 1127548 | 9/1968 | United Kingdom | 128/361 |
| 820819 | 4/1981 | U.S.S.R. | 128/361 |

*Primary Examiner*—Michael H. Thaler
*Attorney, Agent, or Firm*—Kenyon & Kenyon

[57] ABSTRACT

A method and apparatus for delivering a fetus, particularly a human fetus, are disclosed. One or more sheets of material are disposed in the maternal delivery canal between a part of the fetus and the canal wall. An appropriate surface or surfaces have a low coefficient of friction so that friction between the fetus part and the canal wall is reduced during delivery. In the case of delivery of a human fetus, according to one embodiment, two sheets of material having low coefficient of friction surfaces are arranged side-by-side with the low friction surfaces facing each other, and inserted into the vagina surrounding the fetal head and separating it from the vaginal wall. An inner sheet contacts and surrounds the fetal head while an outer sheet contacts the inner sheet and the vaginal wall. During delivery of the fetal head, the low friction surface of the inner sheet slides substantially frictionlessly relative to the low friction surface of the outer sheet so that friction otherwise present between the fetal head and the vagina is eliminated or substantially reduced. The two sheets can be formed by a single folded sheet.

14 Claims, 25 Drawing Figures

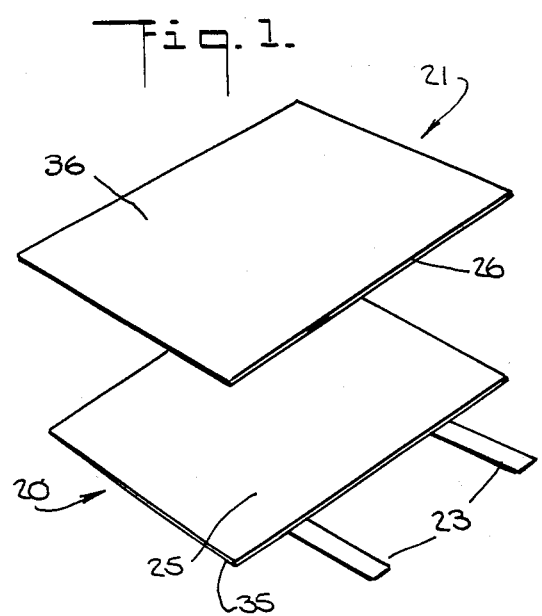
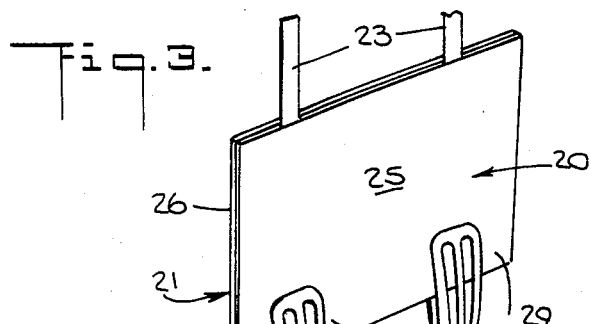
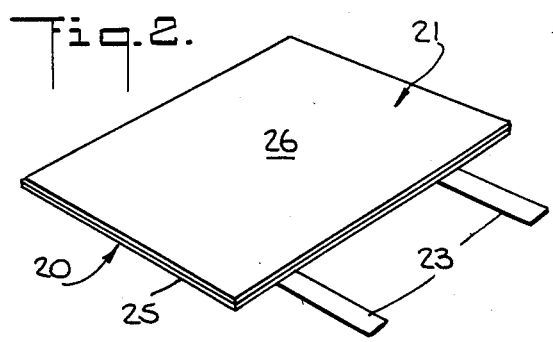
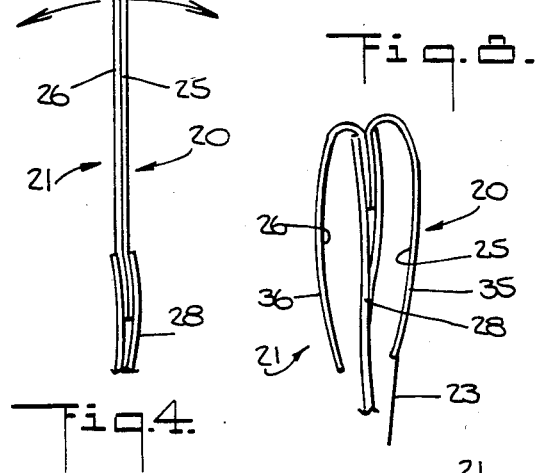
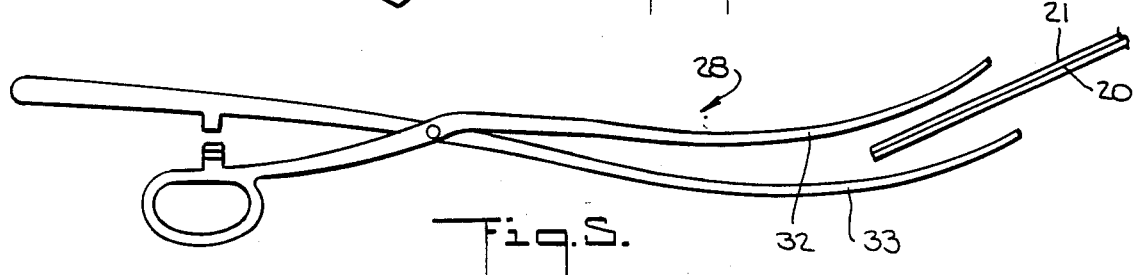
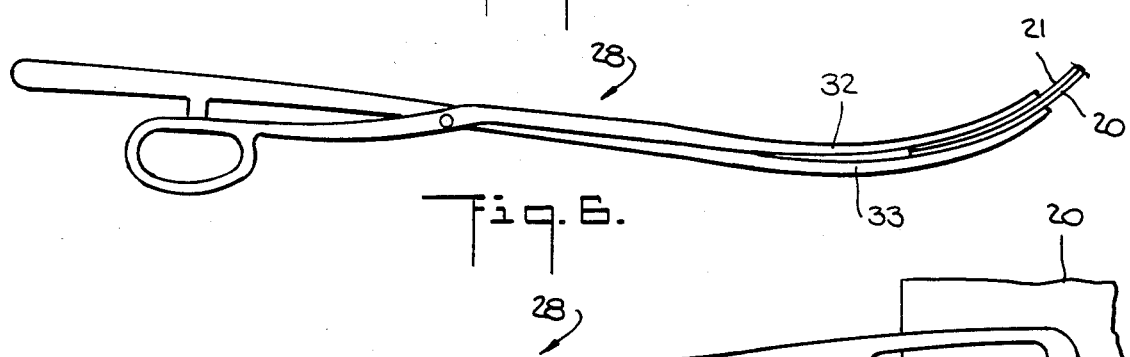
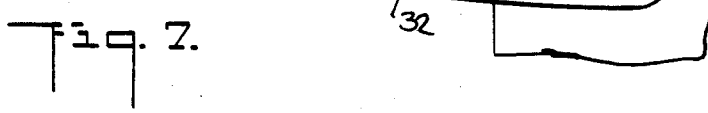

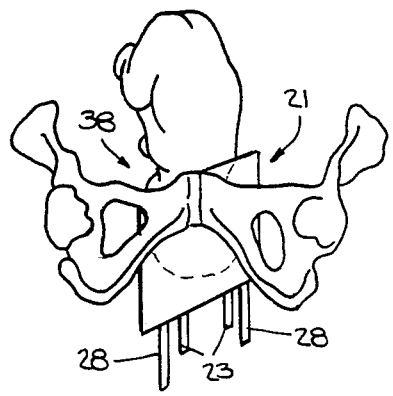
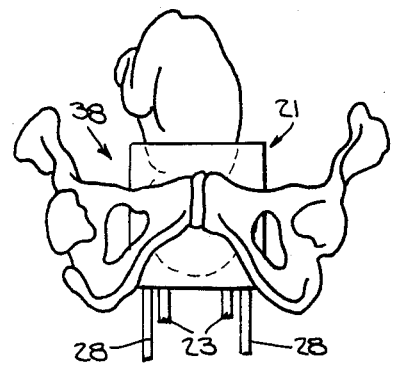
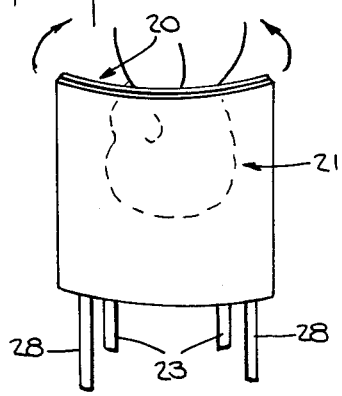
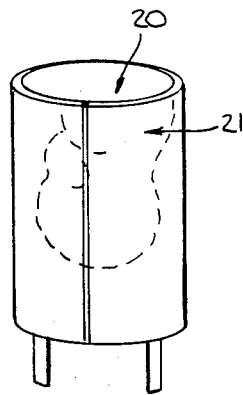
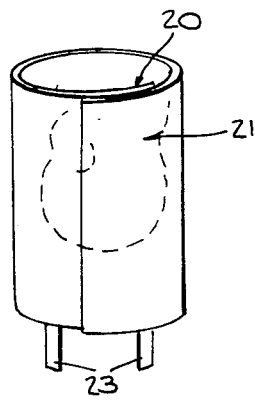
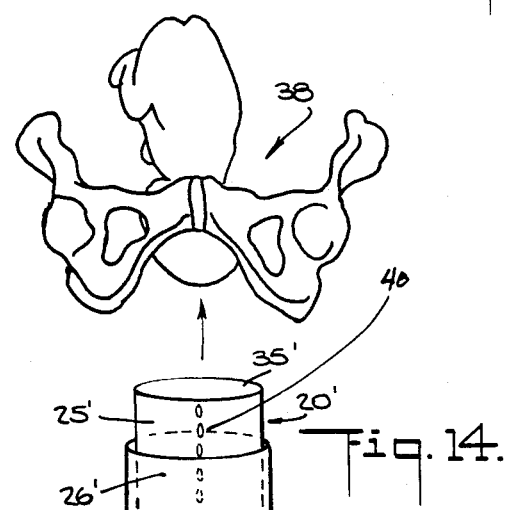
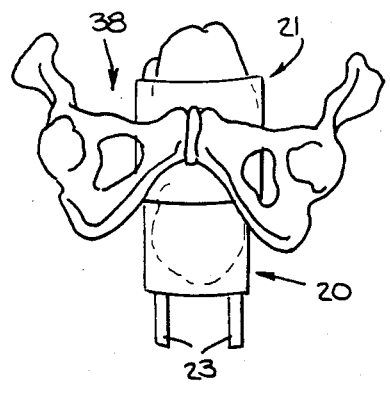

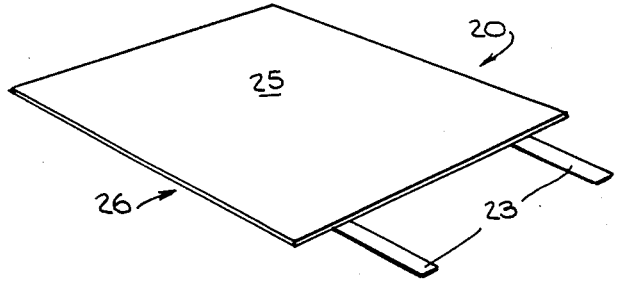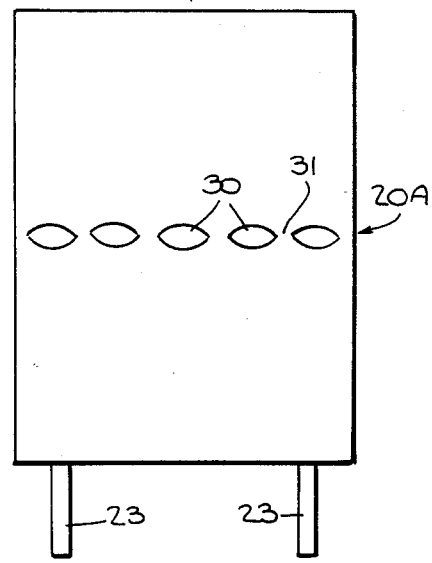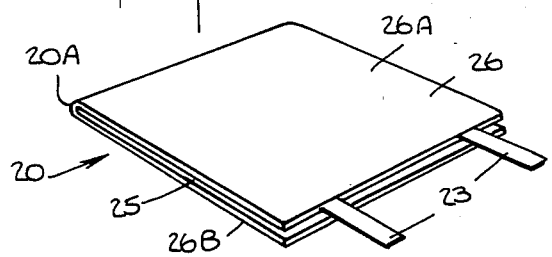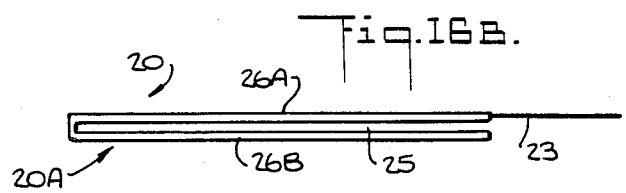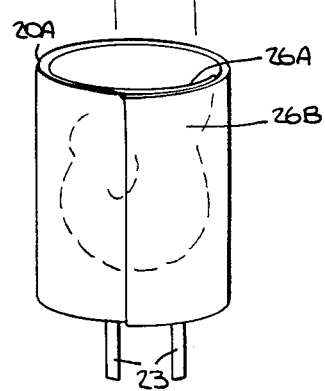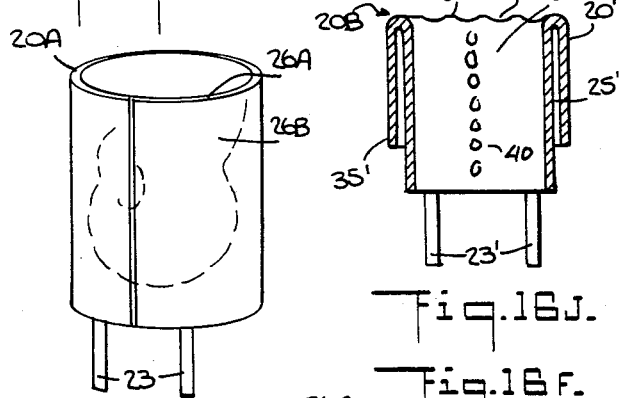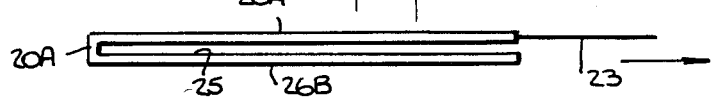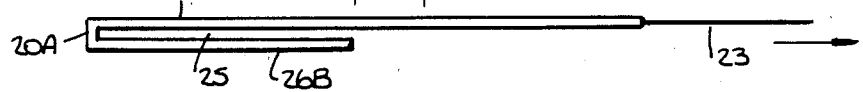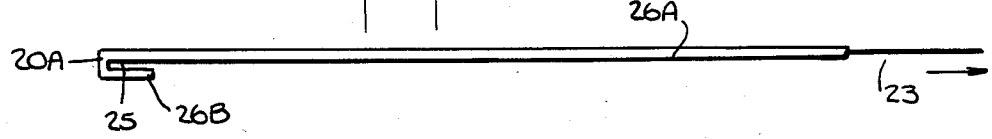

METHOD OF DELIVERING A FETUS

BACKGROUND OF THE INVENTION

The present invention relates to a method of and apparatus for delivering a fetus from a viviparous animal, particularly a human.

At one time and to a certain extent today, the use of forceps and/or the use of what is known as vacuum extraction were prevalent in certain circumstances to assist in the delivery of a fetus, both in human obstetrics and in veterinary deliveries. With respect to humans, procedures employing forceps and/or vacuum extraction attempted to extract a fetus by its head from the vagina without causing injury to the fetus or its mother. See, for example, "Williams Obstetrics", 16th Edition, Chapter 41, "Forceps Delivery and Related Technics". Both procedures are well known in the art, the forceps procedure being traceable as far back as the thirteenth century. Although well established, both procedures subject both the mother and fetus to the risk of serious injury.

With respect to the use of forceps, although not generally acknowledged or appreciated, compression of the fetal head by the forceps is inevitable which can have a harmful effect on the brain. For example, such compression may cause circulation to be hindered and result in asphyxia and hemorrhaging. Direct injury to the cranial bones, nerves and vessels of the fetal head as well as to the brain itself can also result from the compressive use of forceps on the fetus. Also, the mother's vaginal soft tissue may be injured during a procedure in which forceps are applied to the fetus.

Use of vacuum extraction on the fetus during delivery is thought to be a cause of trauma to the fetal scalp, fetal subgaleal hematomas, fetal scalp lacerations and skin necrosis. Fetal intracranial and intraocular hemorrhages have also been reported as a result of vacuum extraction, as has damage to the vaginal soft tissue of the mother.

There are additional drawbacks to the use of forceps and vacuum extraction in human obstetrical delivery procedures, particularly when the fetal head is not visible and has progressed only to the higher positions in the vagina, such as when the fetal head is above the perineum. The use of forceps in such fetal head positions, known as mid or high forceps procedures, is rare as the procedures are extremely complicated and risky. Thus, forceps are generally applied when the fetal head is already visible during contraction, a position known as low forceps. Vacuum extraction, however, is often used when a fetus is in the higher positions. In addition to the drawbacks discussed above concerning vacuum extraction, use of vacuum extraction to a fetus located in the higher positions delays delivery since creation and application of a vacuum to the fetal head in the higher positions requires about ten minutes. This ten minute delay can be critical in the case of a fetal distress.

Because of the many negative factors described above, currently, caesarean sections are being resorted to as an alternative to forceps and vacuum extraction procedures. Caesarean section deliveries are also not without risks and complications, as is also well documented in the art.

The invention disclosed in this application avoids the drawbacks discussed above and facilitates delivery of a fetus, particularly a human fetus.

SUMMARY OF THE INVENTION

It is an object of the invention disclosed herein to facilitate delivery of a fetus while avoiding injury to the fetus, particularly to its head, and to the mother.

It is another object of the invention to deliver a fetus without applying compressive forces and tensile forces heretofore used in forceps and vacuum extraction procedures and other procedures which grip the fetal head and pull it from the maternal passage.

It is another object of the invention to deliver a fetus without gripping the fetal head with instruments such as those noted above.

The applicant has come to realize that the principal force opposing the human fetal delivery process is caused by friction between the fetal head, and particularly the fetal face, and the soft, but elastic, tissue of the human maternal passage at the bony pelvis, i.e., the perineum region. This opposing force is further aggravated by the resistance of the maternal canal to passage of the fetus and by the irregular configuration of a fetal head. The average fetal head diameter is smaller than a corresponding bony pelvis diameter by about 2-4 cm. The fetal head, of course, exhibits the largest diameter of the fetus. Therefore, completion of delivery is easier once the fetal head has protruded. In the event that the bony pelvis diameter is smaller than the diameter of the fetal head, delivery is effected by a caesarean section. Moreover, when significant frictional forces between a fetal head and the vagina wall at the bony pelvis are encountered and it is perceived that conventional methods would subject the fetus and/or mother to undue risks, doctors in such cases heretofore readily resorted to delivery by caesarean section.

Procedures using forceps, vacuum extraction and other gripping instruments utilize the same basic theory of mechanical extraction of a fetus with an applied force greater than the force opposing delivery. On the other hand, the underlying principal of the invention disclosed herein involves facilitating delivery of a fetus by reducing the forces opposing delivery. The applicant has discovered that eliminating or at least substantially reducing the frictional forces between the fetus and the maternal passage eliminates most of the force opposing delivery, and in the case of humans particularly at the bony pelvis area of the vagina. In accordance with the invention, the natural opposing frictional forces are most advantageously reduced at the regions of contact between the maternal passage and the fetal head and fetal face.

Tne inventive method disclosed herein is physiological in nature and assists the natural maternal efforts, e.g., muscular contractions which push the fetus, as distinguished from procedures in which instruments such as forceps and vacuum extractors apply force to or otherwise grip the fetal head in order to pull the fetus out. Viewing the fetus as a separate body intended to be expelled, in a mechanical sense, from a maternal canal and noting that certain natural forces oppose this process while others aid it, the inventive method seeks to minimize the natural opposing forces so that the natural aiding forces can perform more effectively.

In accordance with the inventive method, the frictional forces at the regions of contact between the maternal passage and the fetus are reduced by use of at least one sheet of material disposed between the fetus or a part of the fetus and the maternal passage. The at least one sheet either moves with the fetus as it is being delivered, readily sliding with respect to the maternal passage, or remains in the maternal passage, at least initially, while the fetus or fetus part slides readily relative to the sheet. Where more than one sheet is used, or a single sheet is folded, two surfaces having low coefficients of friction with respect to each other are juxtaposed and readily slide with respect to one another. One sheet remains, at least initially, in the maternal passage while the other sheet slides with the fetus or fetus part out of the maternal passage.

The method of the invention is applicable to delivering a fetus from a viviparous animal, and in one embodiment the method comprises the steps of arranging a sheet of flexible material, a first surface of which has a low coefficient of friction, at least partially in the delivery canal of a viviporous animal with a portion of a second surface of the sheet substantially surrounding at least a part of the fetus so that the sheet substantially separates at least said part of the fetus and the wall of the canal with part of said second surface contacting the fetus and part of said first surface contacting the wall of the canal, and causing the portion of the sheet surrounding said fetus part to be removed from the canal together with said fetus part. Alternatively, the low coefficient of friction surface can surround the fetus and the sheet can be held in the maternal passage, at least initially, while the fetus is being removed from the canal.

In another embodiment of the invention, the method comprises the steps of arranging two sheets of flexible material side-by-side at least partially in the delivery canal of the animal with the two sheets substantially surrounding at least a part of the fetus so that the sheets substantially separate at least said fetus part and the wall of the canal. Each of the sheets has a low coefficient of friction surface and a surface having a higher coefficient of friction; respective low friction surfaces of the two sheets are in a facing relationship when the sheets are in the canal with the higher coefficient of friction surface of the inner sheet contacting the fetus and the higher coefficient of friction surface of the outer sheet contacting the wall of the canal. The inner sheet is caused to be removed from the canal together with the fetus part while the outer sheet remains at least partially in the canal so that the inner sheet slides past the outer sheet as the fetus part is being removed from the canal.

In another embodiment, using two sheets of flexible material both surfaces of each of the two sheets are low coefficient of friction surfaces.

In still another embodiment of the invention, the method comprises the steps of arranging a folded sheet of flexible material, the surface interior of said fold having a low coefficient of friction, at least partially in the delivery canal of the animal with a portion of the surface exterior of said fold substantially surrounding at least a part of the fetus so that the sheet substantially separates at least said part of the fetus and the wall of the canal with part of said exterior surface contacting the fetus and part of said exterior surface contacting the wall of the canal, and causing the portion of the sheet surrounding said fetus part to be removed from the canal together with said fetus part while the portion of the sheet in contact with the wall of the canal remains at least partially in the canal so that said portions of the sheet slide past each other as said fetus part is being removed from the canal.

In another embodiment using a single, folded sheet of flexible material, both surfaces of the single sheet can be low coefficient of friction surfaces.

In the embodiment using two sheets, which have respective low and higher coefficient of friction surfaces, the two sheets can be inserted into the canal as follows. The two sheets of material are initially arranged side-by-side with the two low friction surfaces facing away from each other. Tne sheets are then clamped together at two spaced locations lying along a common edge of each sheet by forceps-type instruments used to insert the sheets into the canal. Each clamped sheet is next pivoted about its clamped edge so that the two low friction surfaces are now facing each other with the clamp part of the instruments between the two sheets. The clamped, pivoted sheets are then inserted into the canal using the forceps-type instruments. Tne procedure for insertion is the same when both surfaces of each sheet are low coefficient of friction surfaces.

The single sheet can be inserted as follows. The sheet is first folded over itself with the two low friction surfaces facing away from each other. The folded edge is then clamped by the forceps-type instruments. The sheet is then unfolded and reverse folded with the low friction surfaces facing each other and the clamp part of the instruments between the two flaps formed by so folding the sheet. The procedure for insertion of a single sheet of which botn surfaces are low coefficient of friction surfaces is the same.

The clamped, pivoted sheets (or folded sheet can be inserted into the canal by inserting one end of the side-by-side sheets into the delivery canal of the animal between the fetus part and the wall of the canal, then inserting the remainder of the side-by-side sheets into the delivery canal of the animal between the fetus part and the wall of the canal with the sheets extending along a portion of the fetus part, and then substantially surrounding the fetus part with the side-by-side sheets so that the sheets substantially separate the fetus part and the wall of the canal with the surface of the inner sheet having the higher coefficient of friction (if the coefficients of friction are unequal) contacting the fetus part and the surface of the outer sheet having the higher coefficient of friction (if the coefficients of friction are unequal) contacting the wall of the canal.

The outer sheet or exterior folded sheet is maintained in the canal by frictional effects between the wall of the canal and the surface of the outer sheet having the higher coefficient of friction (if the coefficients of friction are unequal), as the inner sheet is being removed. The inner sheet can be provided with tabs which can be grasped to pull the inner sheet out of the canal as the fetus is being delivered.

Although the inventive method has application to delivery of a fetus from many viviparous animals, it has particular application to the delivery of a human fetus. In such a case, the sheet or sheets are arranged in the perineum region of the vagina surrounding at least part of the head of the fetus so that the sheet or sheets substantially separate the fetus head and the wall of the vagina in the perineum region. The manner of insertion described above in which one end and then the other end of the juxtaposed sheets are inserted is preferred when the method is used for human childbirth.

The invention also resides in providing the sheets in one or more of the configurations described above and hereinafter.

Other benefits of the invention include minimal material and instrumentation costs. Further, the sheet or sheets used in this method are of low cost and can be disposed of after use. Tne inventive method can facilitate a significant number of human deliveries, which now involve the use of forceps. The invention will also enable cases in which ceasarian sections are to be performed to be selected more judiciously. Moreover, the invention can be used not only in low forceps positions but also in mid and high forceps positions as well. Also, the method reduces the need for special training or skills on the part of personnel assisting the birth process, particularly in veterinary medicine. Thus, in veterinary medicine, about 15 to 20 percent of bovine deliveries which were formerly assisted by a veterinarian can be made by untrained personnel such as farmers using the invention.

The above and other objects, features, aspects and advantages of the present invention will be more readily perceived from the following description of the preferred embodiments thereof when considered with the accompanying drawings and appended claims.

BRIEF DESCRIPTION OF THE DRAWINGS

The present invention is illustrated by way of example and not limitation in the figures of the accompanying drawings in which like numerals indicate similar parts and in which:

FIG. 1 is a side perspective view of apparatus according to the invention used in carrying out the method of the invention depicting two sheets of material;

FIG. 2 is a side prospective view showing the sheets of FIG. 1 arranged side-by-side as a starting point for practice of one embodiment of the method;

FIG. 3 is a front view of the sheets depicted in FIG. 1 clamped together with forceps-type instruments;

FIG. 4 is a side view of the sheets depicted in FIG. 1 in the condition depicted in FIG. 3;

FIG. 5 is a side view of one of the forceps-type instruments depicted in FIGS. 3-4 in its open condition;

FIG. 6 is a side view of the instrument depicted in FIG. 5 in its closed and locked condition with the sheets clamped therein;

FIG. 7 is a front view of the instrument depicted in FIG. 5 in its closed and locked condition with the sheets clamped therein;

FIG. 8 is a side view of the sheets depicted in FIG. 1 after they have been pivoted from the condition depicted in FIGS. 3-4 to enclose part of the forceps-type instruments;

FIG. 9 is a schematic view of a portion of the human female anatomy depicting the region of the pelvis with the fetus emerging during delivery and the sheets of FIG. 1 being inserted between the fetus head and the vagina wall;

FIG. 10 is a schematic view similar to that of FIG. 9 after the sheets have been inserted into the vagina;

FIG. 11 is a schematic perspective view of the fetal head and the sheets in the position of FIG. 10;

FIG. 12 is a perspective schematic view of the sheets enclosing the fetal head in the vagina after the sheets have been wrapped around the fetal head;

FIG. 13 is a perspective schematic view similar to that of FIG. 12 with the sheets in an overlapping arrangement after being wrapped around the fetal head;

FIG. 14 is a schematic view similar to that of FIG. 9 depicting another embodiment of sheet construction, i.e., one of a pair of flexible cylinders or sleeves, being inserted according to another embodiment of the invention; and FIG. 15 is a schematic view corresponding to that of FIG. 10 depicting the fetal head emerging from the vagina together with one of the sheets.

FIG. 16A is a side perspective view of apparatus according to the invention used in carrying out the method of the invention depicting one sheet of material;

FIG. 16B is a profile showing the sheet of FIG. 16A folded;

FIG. 16C is a side perspective view showing the sheet of FIG. 16A folded;

FIGS. 16D, 16E are perspective schematic views of the sheet of FIG. 16C, corresponding to FIGS. 12, 13 respectively;

FIGS. 16F, 16G, 16H are profiles showing in schematic fashion successive instants of the movement of sheet portions 26A, 26B of the sheet of FIG. 16C;

FIG. 16I, is a front view of a sheet in accordance with FIG. 16A having perforations; and FIG. 16J is a cross-section view of the sleeve 20' depicted in FIG. 14, folded upon itself.

DESCRIPTION OF THE PREFERRED EMBODIMENTS

Referring more particularly now to the drawings, preferred embodiments of the method according to the invention and apparatus for carrying out the method are illustrated. While the method and apparatus are illustrated and described in connection with the delivery of a human fetus, the method and apparatus are applicable to delivery of other fetuses as well.

As shown in FIG. 1, two sheets 20, 21 of material which are used in the delivery method disclosed herein are depicted. The two sheets are juxtaposed, as described below, and inserted into the vagina to surround the fetal head and separate it from the vaginal wall as also described below. An inner of the two sheets (corresponding to sheet 20 in FIG. 1) is removed from the vagina with the fetal head while still surrounding it as the outer sheet remains in the vagina during delivery of the fetal head. The surfaces of the two sheets which are in contact with each other have a low coefficient of friction so that the two sheets easily slide relative to each other. Thus, as the fetal head emerges from the vagina, it is substantially not in contact with the vaginal wall, but rather with one of the two sheets. As a result, the fetal head is not subjected to frictional forces between it and the vagina wall otherwise present as the head progresses through the vagina.

The two sheets 20, 21 are made of a flexible, thin material. At least one of the surfaces 25, 26 of each sheet has a low coefficient of friction. The opposite surface 35, 36 of each sheet can have the same coefficient of friction or, alternatively, can be softer, more porous, or slightly rougher than the low friction coefficient surface, and so have a higher coefficient of friction. The low friction surfaces face each other when the juxtaposed sheets are inserted into the vagina, as will be described below. The sheets when used for human childbirth are made of a biologically safe material, for example, polyurethane films, polyester films (some of which are available under the trademark Mylar), polymerized tetrafluoro-ethylene films (some of which are available under the trademark Teflon), polyethylene terephthalate film (PET), polyethylene films and others. Preferably, both sheets, or at least the sheet which is removed with the fetal head, are not made of an elastomeric material so tnat stretching of one or both of the sheets is avoided. Tnis enhances sliding of the two sheets relative to each other. The sheets are advantageously provided as a sterile, disposable product. The thickness and flexibility of the sheets will vary with the particular material used. For example, for sheets made of the foregoing materials, a suitable thickness is 0.1 cm. For use in delivery of a human fetus, suitable dimensions for the sheets are 25 cm. in length and 10 cm. in width. Thinner materials are preferred because of the limited clearance between the fetal head and the vagina in the region of the bony pelvis, although some rigidity to cause the sheet removed with the fetal head to spring open as the head emerges from the vagina, thereby not impeding the newly born child's first breaths, and as well to decrease the natural tendency of the vaginal wall to conform to the contours of the fetal face, is desirable. The sheets can be provided made entirely of a material having a low coefficient of friction; alternatively, one surface thereof can be treated mechanically or chemically to increase its coefficient of friction, or be coated on one surface with a material such as those sold under the Teflon trademark having a low coefficient of friction, the other surface being softer, more porous or rougher. As an alternative or in addition to providing the sheets with the low friction surfaces, a lubricant such as a sterile oil can be applied between the sheets.

In summary, the low friction "bearing" so provided between the two sheets in most instances will provide sufficient reduction of forces in the vagina opposing delivery to permit a spontaneous delivery. Thin tabs 23 can be secured to the removable sheet (sheet 20 in FIG. 1) so that a pulling force, which essentially has no effect on the fetal head, can be applied to the sheet.

A method of inserting the two sheets into the vagina will now be described with respect to FIGS. 2-13. The two sheets 20 and 21 are placed in a side-by-side relationship as shown in FIG. 2. As discussed above, at least two surfaces have a low coefficient of friction which in FIG. 2 are arranged as the outer surfaces 25, 26 of the sheets. The edges of the two juxtaposed sheets are clamped between the jaws of forceps-type instruments 28 as shown in FIGS. 3-4. The instruments clamp the two sheets at two spaced locations 29, 30 which are also spaced inwardly from the ends of the sheets, for reasons which will be described below. As is conventional, the forceps 28 is about twenty-four inches long and includes hinged jaws 32, 33 which can be locked in the closed position depicted in FIG. 6 to clamp the two sheets together. FIG. 5 shows the jaws of the forceps in an open condition between which the sheets are being inserted. In FIGS. 6 and 7, the forceps are shown locked with the sheets clamped between the locked jaws as mentioned above. The forceps 28 or other holders can be made disposable or to be sterilized and reused.

Referring now to FIG. 4, each of the clamped sheets is moved in the direction of the respective arrow while the sheets remain clamped by the forceps and pivoted until the sheets are again side-by-side as shown in FIG. 8 with both forceps extending between the sheets and protruding from the edges of the sheets opposite to the clamped edges. The low friction surfaces 25, 26 of the sheets are now facing each other and the sheets are ready to be inserted into the vagina. As indicated above, the outer surfaces, designated 35, 36 in FIG. 8, can have a higher coefficient of friction, but one not so large that insertion of the sheets will be impeded by friction between the sheets themselves and the vaginal wall and/or the fetal head.

Referring to FIG. 9, one end of the FIG. 8 clamped sheets is inserted into the vagina by insertion of one of the forceps into the vagina between the fetal skull and the wall of the vagina in the perineum area of the vagina designated by 38. About 40% of the sheets can be inserted with one forceps. Then, the other forceps is used to insert the other end of the two sheets into the vagina as depicted schematically in FIG. 10 with the sheets flexed into a more or less semi-circular condition, as schematically depicted most clearly in FIG. 11. The forceps are introduced using the same techniques employed in the introduction of a single blade of an obstetrical forceps. After both forceps are in the vagina with the two sheets partially surrounding the fetal head and separating it from part of the vaginal wall, the two forceps are moved about the uncovered part of the fetal head along a circular path denoted by the arrows in FIG. 11 until the two sheets form a cylinder as shown in FIGS. 12 or 13. The two sheets can be formed into a partially opened cylinder as shown schematically in FIG. 12 or a closed cylinder as shown schematically in FIG. 13 in which the edges of the sheets overlap. The two forceps are spaced from the ends of the sheets so that the sheets can be butted (FIG. 12) or overlapped (FIG. 13). After the sheets have been positioned surrounding the fetal head, the forceps are unlocked and removed from the vagina.

The two facing and contacting surfaces 25, 26 of the sheets form a low friction bearing which reduces the natural frictional forces opposing delivery of the fetus. The outer surface 36 of the outer sheet 21 remains relatively fixed due to the friction between it and the vaginal tissue surrounding the perineum opening. The inside surface 35 of the inner sheet 20 will not slide with respect to the fetal head because of frictional forces generated between those two surfaces. Friction is essentially eliminated only between the outside surface 25 of the inner sheet 20 and the inside surface 26 of the outer sheet 21. As a result, the two sheets slide easily with respect to each other but each individual sheet encounters friction with the vaginal wall or fetal head. Thus, as the natural delivery forces seek to expel the fetus, the fetal head wrapped in the inner sheet 20 passes through the area of high friction at the perineum opening because of the reduced frictional forces between the two sheets. Tabs 23 connected to the inner sheet will protrude from the vagina when the sheets are in place. This allows a pulling force to be applied to the tabs to assist in the delivery process. The sheets can also be provided without the tabs as the tabs are not absolutely essential to practising the inventive method.

Referring to FIG. 15, the fetal head is shown emerging from the vagina wrapped in the inner sheet 20. The tabs 23 can be pulled as described above, to assist in the natural delivery process. In many instances, the fetal head will simply emerge with the inner sheet under the natural muscular action of the mother without the need to apply any external force.

In another embodiment of sheet construction, shown in FIG. 14, each sheet 20', 21' is provided in the form of a preformed sleeve of generally cylindrical shape, the sleeve 21' having a larger diameter. Foreceps 28 are used, in a manner similar to that described above, to insert each sleeve, one at-a-time, sleeve 20' first, or to insert both sleeves simultaneously. The inner surface 35' of sleeve 20' has a higher than or the same coefficient of friction as its outer surface 25'. The outer surface 26' of sleeve 21' has a higher than or the same coefficient of friction as its inner surface 36'. When inserting the sleeves one at a time, upon insertion of the sleeve 20' first, its inner surface is in contact with a fetal part, e.g., the fetal head. Sleeve 21' is then inserted or slipped on over the sleeve 20', so that the low coefficient of friction inner surface 36' of the former is in contact with the low coefficient of friction outer surface 25' of the latter. The sleeve 20' may be provided with tabs 23' and delivery effected as described above by relative movement of inner sleeve 20' with reference to outer sleeve 21'.

Referring to FIGS. 16A–16I, which depict another embodiment of apparatus, according to the invention, used in carrying out the method of the invention, a sheet 20 (FIG. 16A) has the characteristics described with reference to FIG. 1. The sheet 20 has a first surface 25 having a low coefficient of friction, a second surface 26, having the same or a higher coefficient of friction, and tabs 23 for the purpose described above.

The sheet 20 is folded upon itself (FIG. 16B) so that the surface 25 is interior of the fold 20A and the surface 26 is exterior of the fold 20A. When the sheet 20 is folded, the surface 26 (FIG. 16C) has two portions 26A, 26B, which have been depicted as of the same size. However, this proportion is not critical and portion 26A may be greater or less than portion 26B, depending upon the particulars of the specific delivery to be effected.

Utilizing techniques similar to those described above, with reference to FIGS. 8–15, the folded sheet 20 is inserted in the delivery canal so that the portion 26A exterior of the fold 20A substantially surrounds a fetal part, e.g., the fetal head (FIGS. 16D, 16E), while the portion 26B contacts the wall of the delivery canal.

In delivery, tabs 23 are grasped and pulled outward of the delivery canal (e.g., to the right as depicted in FIG. 16F) Because the surface 25 has a low coefficient of friction, the sheet portion 26A in contact with the fetal part slides past the sheet portion 26B in contact with the delivery canal. Successive instants of this motion are depicted schematically in FIGS. 16F–16H. The two portions 26A, 26B slide easily with respect to each other but each individual portion encounters friction with the fetal head (i.e., portion 26A) or with the vaginal wall (i.e., portion 26B) Thus, as the natural delivery force seeks to expel the fetus, the fetal head wrapped in the sheet portion 26A passes through the area of high friction at the perineum opening because of the reduced frictional forces at surface 25 between the two sheet portions. Tabs 23 connected to the sheet 20 protrude from the vagina when the sheet is in place, e.g., butted as shown in FIG. 16D or overlapped as shown in FIG. 16E. This allows a pulling force to be applied to the tabs to assist the delivery process. The sheet 20 can also be provided without the tabs, in which case forceps instruments, e.g., the forceps of FIGS. 5–7, are used to grasp and pull sheet portion 26A.

Moreover, the sheet 20 can be perforated at the region of fold 20A, as depicted in FIG. 16I, with large perforations 30 having small islands 31 therebetween. When folded and inserted in place as described above, rotational motion of the fetus during delivery will tend to fracture the islands 31, thereby forming two separate sheets and tnus enhancing the relative movement of the sheet surfaces 25.

In another embodiment of sheet construction schematically depicted in cross-section in FIG. 16J, a single sleeve 20' of the kind described with reference to FIG. 14 is rolled upon itself so that the inmost and outmost portions of the resulting cylindrical shape are comprised of portions of the higher (or equal) coefficient of friction surface 35', whilst adjacent portions of low coefficient of friction surface 25' are in contact. It is apparent that this construction is analogous to the folded single sheet construction of FIGS. 16A, 16C and may be provided with large perforations 30 having small islands 31 therebetween, of the kind and for the purpose described above with reference to FIG. 16I. The rolled-up sleeve 20' is inserted in a manner similar to that described above with reference to FIG. 14. Upon insertion, the two portions of surface 35' are in contact with the vaginal wall and fetal part. In delivery, the two portions of low coefficient of friction surface 25 slide easily with respect to each other whilst the portion of surface 35', in contact with the vaginal wall, stays relatively in place; the motion is analogous to that depicted with reference to FIGS. 16F to 16H.

In another embodiment of sheet construction, a single sleeve 20' as depicted in FIG. 14 and having an outer low coefficient of friction surface 25' and an inner higher or equal coefficient of friction surface 35' can be inserted without folding, all as more particularly described with reference to FIG. 14. In the delivery method utilizing this apparatus, the low coefficient of friction surface 25' is in contact with the vaginal wall or delivery canal, whilst the higher or equal coefficient of friction surface 35' is in contact with the fetal part. The natural delivery force seeking to expel the fetus can then be aided by application of a pulling force to the tabs 23.

To facilitate removal of the sleeve construction of FIGS. 14 and 16J from the fetal part, after delivery, the sleeve 20' can be provided with one or more longitudinal rows of perforations 40 or alternatively with one or more longitudinal slits (not shown).

In another embodiment of sheet construction, a single sheet as depicted in FIG. 16A can be inserted without folding, so that the first surface 25 having a low coefficient of friction is in contact with the delivery canal, while the second higher or equal coefficient of friction surface 26 is in contact with the fetal part. The natural delivery force seeking to expel the fetus can then be aided by application of a pulling force to the tabs 23.

It is to be understood that "low" and "higher" used herein with reference to coefficients of friction are relative terms and that for the purpose of obtaining the benefits of this invention the coefficients of friction of the surfaces of the flexible materials used to effect delivery may be the same or different from each other.

Certain changes and modifications of the embodiments of the invention disclosed herein will be readily apparent to those skilled in the art. It is the applicant's intention to cover by his claims all those changes and modifications which could be made to the embodiments of the invention herein chosen for the purpose of disclosure without departing from the spirit and scope of the invention.

What is claimed is:

1. A method of delivering a fetus from a viviparous animal comprising the steps of arranging two sheets of flexible material each of which has a low coefficient of friction surface side-by-side at least partially in the delivery canal of the animal with respective low friction surfaces of the two sheets in a facing relationship and the two sheets substantially surrounding at least a part of the fetus so that the sheets substantially separate at least said part of the fetus and the wall of the canal with an inner sheet contacting the fetus and an outer sheet contacting the wall of the canal, causing the inner sheet to be removed from the canal together with said fetus part while the outer sheet remains at least partially in the canal so that the inner sheet slides past the outer sheet as said fetus part is being removed from the canal.

2. The method according to claim 1 wherein, prior to inserting the sheets into the canal:

the two sheets of material are initially arranged side-by-side with the two low friction surfaces facing away from each other;

the sheets arranged with the two low friction surfaces facing away from each other are clamped together at two spaced locations lying along a common edge of each sheet by forceps-type instruments used to insert the sheets into the canal;

each clamped sheet is pivoted about its clamped edge so that the two low friction surfaces are facing each other; and the clamped, pivoted sheets are inserted into the canal using the forceps-type instruments.

3. The method of claim 1 wherein the clamped, pivoted sheets are inserted into the canal by inserting one end of the side-by-side sheets into the delivery canal of the animal between said fetus part and the wall of the canal, then inserting the remainder of the side-by-side sheets into the delivery canal of the animal between said fetus part and the wall of the canal with the sheets extending along a portion of said fetus part, and then substantially surrounding said fetus part with the side-by-side sheets so that the sheets substantially separate said fetus part and the wall of the canal with an inner sheet contacting the fetus part and an outer sheet contacting the wall of the canal.

4. The method according to claim 1 wherein each sheet is provided in the form of a sleeve of cylindrical shape, the contiguous surfaces of said sleeves comprising surfaces of a low coefficient of friction, whilst the surfaces of said sleeves in respective contact with said wall and fetal part have higher or equal coefficient of friction surfaces .

5. The method according to claim 1 wherein the inner sheet includes tabs which can be grasped to pull the inner sheet out of the canal as the fetus is being delivered.

6. The method according to claim 1 wherein the outer sheet is maintained in the canal as the inner sheet is being removed by holding it with a forceps-type instrument.

7. An obstetrical method for delivering a human fetus comprising the steps of arranging two sheets of flexible material each of which has a low coefficient of friction surface side-by-side at least partially in the vagina of the mother in the perineum region of the vagina with a respective low friction surface of each sheet in a facing relationship and the two sheets surrounding at least part of the head of the fetus so that the sheets substantially separate the head and the wall of the vagina with an inner sheet contacting the head and an outer sheet contacting the wall of the vagina, delivering the fetal head from the vagina together with the inner sheet while the outer sheet remains at least partially in the vagina so that the inner sheet slides past the outer sheet as the fetal head is being delivered.

8. The method according to claim 7 wherein, prior to insertion into the vagina:

the two sheets of material are initially arranged side-by-side with the two low friction surfaces facing away from each other;

the sheets arranged with the two low friction surfaces facing away from each other are clamped together at two spaced locations lying along a common edge of each sheet by forceps-type instruments used to insert the sheets into the vagina, each clamped sheet is pivoted about its clamped edge so that the two low friction surfaces are facing each other; and the clamped, pivoted sheets are inserted using the forceps-type instruments.

9. The method of claim 7 wherein the clamped, pivoted sheets are inserted into the vagina by inserting one end of the side-by-side sheets into the vagina between the fetus head and the wall of the vagina, then inserting the reminder of the side-by-side sheets into the vagina between the fetal head and the wall of the vagina with the sheets extending along a portion of the fetal head, and then substantially surrounding the fetal head with the side-by-side sheets so that the sheets substantially separate the fetal head and the wall of the vagina with an inner sheet contacting the fetal head and an outer sheet contacting the wall of the vagina.

10. The method according to claim 7 wherein each sheet is provided in the form of a sleeve of cylindrical shape, the contiguous surfaces of said sleeves comprising surfaces of a low coefficient of friction, whilst the surfaces of said sleeves in respective contact with said wall and fetal part have higher or equal coefficient of friction surfaces .

11. The method according to claim 7 wherein the inner sheet includes tabs which can be grasped to pull the inner sheet out of the vagina as the fetal head is being delivered.

12. A method of delivering a fetus from a viviparous animal comprising the steps of:

arranging a folded sheet of flexible material, the surface interior of said fold having a low coefficient of friction, at least partially in the delivery canal of the animal with a portion of the surface exterior of said fold substantially surrounding at least a part of the fetus so that the sheet substantially separates at least said part of the fetus and the wall of the canal with part of said exterior surface contacting the fetus and part of said exterior surface contacting the wall of the canal, causing the portion of the sheet surrounding said fetus part to be removed from the canal together with said fetus part while the portion of the sheet in contact with the wall of the canal remains at least partially in the canal so that said portions of the sheet slide past each other as said fetus part is being removed from the canal.

13. An obstetrical method for delivering a human fetus comprising the steps of:

arranging a folded sheet of flexible material, the surface interior of said fold having a low coefficient of friction, at least partially in the vagina of the mother in the perineum region of the vagina with a portion of the surface exterior of said fold surrounding at least part of the head of the fetus so that the sheet substantially separates said head part and the wall part of the vagina with part of said exterior surface contacting said head part and part of said exterior surface contacting the wall of the vagina, delivering the fetal head from the vagina together with the portion of the sheet surrounding said head part while the portion of the sheet in contact with the wall of the vagina remains at least partially in the vagina so that said portions of the sheet slide past each other as the fetal head is being delivered.

14. The method according to claim 12 or 13 wherein said sheet is provided in the form of a sleeve of cylindrical shape, the inner surface thereof having a coefficient of friction equal to or higher than the coefficient of friction of the outer surface thereof, said sleeve being rolled upon itself, and further wherein said rolled sleeve is so arranged in the delivery canal (claim 12) or in the perineum region (claim 13) that portions of said equal or higher coefficient of friction surface are in contact with a part of the fetus and said canal (claim 12) or with part of the fetal head and said perineum region (claim 13).

* * * * *